US006746988B2

(12) United States Patent
Hopkinson et al.

(10) Patent No.: US 6,746,988 B2
(45) Date of Patent: Jun. 8, 2004

(54) SURFACTANT SYSTEMS FOR AGRICULTURALLY ACTIVE COMPOUNDS

(75) Inventors: Michael J. Hopkinson, Greensboro, NC (US); Carolyn E. Moore, Greensboro, NC (US); Jeffrey D. Fowler, Greensboro, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/235,276

(22) Filed: Sep. 5, 2002

(65) Prior Publication Data

US 2003/0050194 A1 Mar. 13, 2003

Related U.S. Application Data

(60) Provisional application No. 60/317,474, filed on Sep. 7, 2001.

(51) Int. Cl.[7] .............................................. A01N 25/30
(52) U.S. Cl. .................. 504/127; 504/128; 504/133; 504/134; 504/136; 504/149; 504/363; 514/777; 514/975
(58) Field of Search ................................ 504/127, 128, 504/133, 134, 136, 149, 363

(56) References Cited

U.S. PATENT DOCUMENTS

| | | | |
|---|---|---|---|
| 4,313,847 A | 2/1982 | Chasin et al. ................ | 252/356 |
| H224 H | 3/1987 | Malik et al. .................... | 71/92 |
| H303 H | 7/1987 | Malik et al. .................... | 514/85 |
| 4,810,279 A | 3/1989 | Martin .......................... | 71/121 |
| 4,888,325 A | 12/1989 | Schroeder et al. ............. | 514/25 |
| 5,258,358 A | 11/1993 | Kocur et al. ................. | 504/205 |
| 5,468,718 A | 11/1995 | Burval et al. ................ | 504/206 |
| 5,516,747 A | 5/1996 | Lachut ......................... | 504/116 |
| 5,731,266 A | 3/1998 | Baker et al. ................. | 504/133 |
| 5,877,112 A | 3/1999 | Roberts et al. .............. | 504/116 |
| 5,885,931 A | 3/1999 | Rogiers et al. ............... | 504/101 |
| 5,928,563 A | 7/1999 | Klima .......................... | 252/364 |
| 6,063,733 A | 5/2000 | Berger et al. ................. | 504/206 |
| 6,121,199 A | 9/2000 | Berger et al. ................. | 504/206 |
| 6,143,830 A | 11/2000 | Utz et al. ..................... | 525/240 |
| 6,165,939 A | 12/2000 | Agbaje et al. ................ | 504/105 |
| 2002/0160916 A1 * | 10/2002 | Volgas et al. ................. | 504/194 |

FOREIGN PATENT DOCUMENTS

| | | |
|---|---|---|
| WO | 96/08150 | 3/1996 |
| WO | 00/07709 | 2/2000 |
| WO | 00/35284 | 6/2000 |
| WO | 00/35863 | 6/2000 |

* cited by examiner

*Primary Examiner*—S. Mark Clardy
(74) *Attorney, Agent, or Firm*—Thomas Hamilton

(57) ABSTRACT

The invention provides surfactant systems comprising alkyl polyglycosides, anionic surfactants and basic compounds. The invention also provides agricultural compositions comprising agriculturally active compounds, alkyl polyglycosides, anionic surfactants and basic compounds. The surfactant systems and agricultural compositions may further comprise nonionic surfactants.

25 Claims, No Drawings

SURFACTANT SYSTEMS FOR AGRICULTURALLY ACTIVE COMPOUNDS

This application claims the benefit of Provisinal Application No. 60/317,474, filed Sep. 7, 2001 now abandoned.

FIELD OF THE INVENTION

The invention provides surfactant systems and agricultural compositions that contain a surfactant system and one or more agriculturally active compounds. The surfactant systems may comprise alkyl polyglycosides, anionic surfactants, basic compounds, and/or nonionic surfactants. The surfactant systems and agricultural compositions exhibit excellent chemical and physical stability as well as tank-mix compatibility properties that are highly desirable for commercial products in the agricultural chemicals industry.

BACKGROUND OF THE INVENTION

The challenge involved in developing commercially acceptable products containing agriculturally active compounds continues to increase due to the rapid emergence of more complex customer and regulatory requirements. The formulation of products containing multiple active ingredients with very different physical properties is increasingly required in the marketplace to provide a broader spectrum of biological activity in a single product offering. These agricultural compositions must exhibit excellent chemical stability and must also maintain a high level of physical stability under a severe range of storage and use conditions. Handling of a liquid product in bulk storage facilities represents a special challenge because the product can be subject to high shear forces at both high and low temperatures. The complexity of the application medium into which the compositions will be blended is also rapidly increasing, creating significant new requirements for compatibility in the application process. This emerging area of performance is critical to customer satisfaction and commercial success with a product since poor compatibility in the final use mixture can cause blockage of sprayer screens and nozzles, preventing proper application of the product. At the same time that the demand on the agrochemical composition performance has been increasing, the number of auxiliary chemicals approved for use in agrochemical compositions by the U.S. EPA has been decreasing due to more stringent standards for the toxicological and ecological properties of these materials.

There is a need in the art for new surfactant systems comprising combinations and applications of auxiliary chemicals which have both unique performance characteristics and a good environmental safety profile. The invention is directed to this, as well as other, important ends.

SUMMARY OF THE INVENTION

The invention provides surfactant systems comprising at least one alkyl polyglycoside; at least one anionic surfactant selected from polyarylphenol polyalkoxyether sulfates and polyarylphenol polyalkoxyether phosphates; at least one basic compound; and, optionally, at least one nonionic surfactant. The at least one anionic surfactant is preferably neutralized to the inflection point in the titration curve with the at least one basic compound. The surfactant systems may further comprise agriculturally active compounds and/or water.

The invention provides agricultural compositions comprising at least one agriculturally active compound; at least one alkyl polyglycoside; at least one anionic surfactant selected from polyarylphenol polyalkoxyether sulfates and polyarylphenol polyalkoxyether phosphates; at least one basic compound; and, optionally, at least one nonionic surfactant. The at least one anionic surfactant is preferably neutralized to the inflection point in the titration curve with the at least one basic compound. The agricultural compositions may further comprise water.

The invention provides flowable concentrates comprising water; at least one agriculturally active compound; at least one alkyl polyglycoside; at least one anionic surfactant selected from polyarylphenol polyalkoxyether sulfates and polyarylphenol polyalkoxyether phosphates; at least one basic compound; and, optionally, at least one nonionic surfactant. The at least one anionic surfactant is preferably neutralized to the inflection point in the titration curve with the at least one basic compound. The flowable concentrates may be, for example, suspoemulsions, aqueous suspension concentrates, aqueous emulsion concentrates, or oil-miscible flowable concentrates.

The invention provides water-in-oil emulsions, capsule emulsions and polymer-stabilized aqueous emulsions comprising water; at least one agriculturally active compound; at least one alkyl polyglycoside; at least one anionic surfactant selected from polyarylphenol polyalkoxyether sulfates and polyarylphenol polyalkoxyether phosphates; at least one basic compound; and, optionally, at least one nonionic surfactant. The at least one anionic surfactant is preferably neutralized to the inflection point in the titration curve with the at least one basic compound.

The surfactant systems, agricultural compositions, flowable concentrates, water-in-oil emulsions, capsule emulsions, and polymer-stabilized aqueous emulsions of the invention may further comprise other additives, such as thickeners, flow enhancers, wetting agents, antifoaming agents, buffers, lubricants, fillers, drift control agents, deposition enhancers, adjuvants, evaporation retardants, frost protecting agents, insect attracting odor agents, fragrances, and the like.

These and other aspects of the invention are described in more detail below.

DETAILED DESCRIPTION OF THE INVENTION

It has been unexpectedly discovered that anionic surfactants neutralized with a basic component, plus an alkyl polyglycoside, and, optionally, a nonionic surfactant, result in surfactant systems that produce agricultural concentrates that exhibit good chemical and physical stability in normal storage conditions and also show good compatibility in a variety of tank mix conditions. Without intending to be bound by any theory of the invention, the surfactants act not only as stabilizers but may also provide an adjuvant effect for some of the agriculturally active compounds.

Any alkyl polyglycoside known in the art can be used in the invention. The alkyl polyglycoside of the invention may have formula (I):

$$R_1O(R_2O)_b(Z)_a \qquad (I)$$

$R^1$ is a monovalent organic radical having from about 6 to about 30 carbon atoms. $R_1$ is preferably a $C_{8-22}$ alkyl or alkenyl group, more preferably a $C_{8-11}$ alkyl group. $R_2$ is a divalent alkylene radical having from about 2 to about 4 carbon atoms. $R_2$ is preferably ethylene or propylene, more preferably ethylene. b is 0 to about 100. b is preferably 0 to about 12, more preferably 0. Z is a saccharide residue having about 5 to about 6 carbon atoms. Z may be glucose, mannose, fructose, galasctose, talose, gulose, altrose, allose, apiose, gallose, idose, ribose, arabinose, xylose, lyxose, or a mixture thereof. Z is preferably glucose. a is an integer from 1 to about 6. a is preferably from 1 to about 3, more preferably about 2.

Preferred compounds of formula (I) are compounds of formula (II):

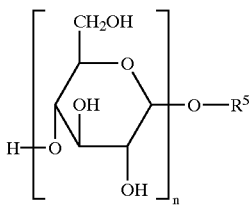
(II)

where n is the degree of polymerization and is from 1 to 3, preferably 1 or 2, and $R^5$ is a branched or straight chain alkyl group having from 4 to 18 carbon atoms or a mixture of alkyl groups having from 4 to 18 carbon atoms.

Exemplary alkyl polyglycosides include APG® 325 (Cognis Corporation, Cincinnati, Ohio) (an alkyl polyglycoside in which the alkyl group contains 9 to 11 carbon atoms and has an average degree of polymerization of 1.6), PLANTAREN® 2000 (Cognis Corporation, Cincinnati, Ohio) (an alkyl polyglycoside in which the alkyl group contains 8 to 16 carbon atoms and has an average degree of polymerization of 1.4), PLANTARN®) 1300 (Cognis Corporation, Cincinnati, Ohio) (an alkyl polyglycoside in which the alkyl group contains 12 to 16 carbon atoms and has an average degree of polymerization of 1.6), AGRIMUL® PG 2067 (Cognis Corporation, Cincinnati, Ohio) (an alkyl polyglycoside in which the alkyl group contains 8 to 10 carbon atoms and has an average degree of polymerization of 1.7), AGRIMUL® PG 2069 (Cognis Corporation, Cincinnati, Ohio) (an alkyl polyglycoside in which the alkyl group contains 9 to 11 carbon atoms and has an average degree of polymerization of 1.6), AGRIMUL® PG 2076 (Cognis Corporation, Cincinnati, Ohio) (an alkyl polyglycoside in which the alkyl group contains 8 to 10 carbon atoms and has an average degree of polymerization of 1.5), ATPLUS® 438 (Uniqema, Inc., Wilmington, Del.) (an alkylpolysaccharide in which the alkyl group contains 9 to 11 carbon atoms), and ATPLUS® 452 (Uniqema, Inc., Wilmington, Del.) (an alkylpolysaccharide in which the alkyl group contains 8 to 10 carbon atoms).

In preferred embodiments, the alkyl polyglycoside is a ($C_{8-10}$ alkyl)-O(glucose)$_2$ (e.g., AGRIMUL® PG 2067); a ($C_{9-11}$ alkyl)-O(glucose)$_2$ (e.g., AGRIMUL® PG 2069); or a mixture thereof.

The alkyl polyglycosides may be used in the compositions of the invention in an amount of about 0.1 to about 8% by weight, preferably in an amount of about 0.5 to 4% by weight.

The anionic surfactants used in the invention may be any known in the art. The anionic surfactants may be polyarylphenol polyalkoxyether sulfates and/or phosphates, $C_{8-18}$ alcohol polyalkoxyether phosphates, carboxylates, and/or citrates, alkyl benzenesulfonic acids, and mixtures thereof.

In a preferred embodiment, the compositions of the invention comprise at least one polyarylphenol polyalkoxyether sulfate and/or at least one polyarylphenol polyalkoxyether phosphate.

In other embodiments, the compositions of the invention comprise at least one anionic surfactant selected from polyarylphenol polyalkoxyether sulfates and polyarylphenol polyalkoxyether phosphates; and at least one anionic surfactant selected from $C_{8-18}$ alcohol polyalkoxyether phosphates, $C_{8-18}$ alcohol polyalkoxyether carboxylates, $C_{8-18}$ alcohol polyalkoxyether citrates, and alkyl benzenesulfonic acids.

In other embodiments, the compositions of the invention comprise at least one anionic surfactant selected from polyarylphenol polyalkoxyether sulfates and polyarylphenol polyalkoxyether phosphates; and at least one anionic surfactant selected from $C_{8-18}$ alcohol polyalkoxyether phosphates and $C_{8-18}$ alcohol polyalkoxyether citrates.

Exemplary polyarylphenol polyalkoxyether sulfates and phosphates include polyarylphenol polyethoxyether sulfates and phosphates, polyarylphenol polypropoxyether sulfates and phosphates, polyarylphenol poly(ethoxy/propoxy)ether sulfates and phosphates, and salts thereof. The term "aryl" includes, for example, phenyl, tolyl, naphthyl, tetrahydronaphthyl, indanyl, indenyl, styryl, pyridyl, quinolinyl, and mixtures thereof. Exemplary polyarylphenol polyethoxyether sulfates and phosphates include distyrylphenol polyethoxyether sulfates and phosphates, and tristyrylphenol polyethoxyether sulfates and phosphates. The polyarylphenol polyalkoxether sulfates and phosphates may have a degree of alkoxylation (e.g., ethoxylation) of between about 1 and about 50, preferably between about 2 and about 40, more preferably between about 5 and about 30. Commercially available polyarylphenol polyalkoxyether sulfates and phosphates include, for example, SOPROPHOR® 4 D 384 (Rhodia Corporation, Cranbury, N.J.) (tristyrylphenol $(EO)_{16}$ sulfate ammonium salt), SOPROPHOR® 3 D 33 (Rhodia Corporation, Cranbury, N.J.) (tristyrylphenol $(EO)_{16}$ phosphate free acid), SOPROPHOR® FLK (Rhodia Corporation, Cranbury, N.J.) (tristyrylphenol $(EO)_{16}$ phosphate potassium salt), DEHSCOFIX® 904 (Albright & Wilson Americas, Inc., Glen Allen, Va.) (tristyrylphenol polyethoxylated ether phosphate triethanolamine salt), HOE® S 3475 (Hoechst) (tristyrylphenol polyethoxylated ether phosphate triethanolamine salt), and SOPROPHOR® RAM/384 (tristyrylphenol polyethoxylated ether sulfate neutralized with polyethoxylated oleylamine). In other embodiments, the polyarylphenol polyalkoxyether sulfates and phosphates may be mono-arylphenol polyalkoxyether sulfates and phosphates, such as styrylphenol polyethoxyether sulfates and phosphates.

Exemplary $C_{8-18}$ alcohol polyethoxyether phosphates, carboxylates and citrates include STEPFAC® 8180 (Stepan Corporation, Northfield, Ill.) (tridecylalcohol $(EO)_3$ phosphate), STEPFAC® 8181 (Stepan Corporation, Northfield, Ill.) (tridecylalcohol $(EO)_6$ phosphate), STEPFAC® 8182 (Stepan Corporation, Northfield, Ill.) (tridecylalcohol $(EO)_{12}$ phosphate), EMCOL® CN-6 (Cromptom Corporation, Greenwich, Conn.) (tridecylalcohol $(EO)_6$ carboxylate), BIOSOFT® S100 (Stepan Corporation, Northfield, Ill.) (dodecylbenzene sulfonic acid), and WITCONATE® 1298 (Crompton Corporation, Greenwich, Conn.) (dodecylbenzene sulfonic acid). The $C_{8-18}$ alcohol polyethoxyether phosphates, carboxylates and citrates may have a degree of ethoxylation of between about 1 and about 25, preferably between about 1 and about 20.

Other anionic surfactants may also be included in the agricultural compositions and surfactant systems of the invention. Such anionic surfactants include, for example, $C_{8-20}$ alkyl carboxylates including fatty acids, $C_{8-20}$ alcohol sulfates, $C_{8-20}$ alcohol phosphate mono- and diesters, $C_{8-20}$ alcohol and ($C_{8-20}$ alkyl)phenol polyoxyethylene ether carboxylates, sulfates and sulfonates, $C_{8-20}$ alcohol and ($C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, and $C_{8-20}$ acyl glutamates, sarcosinates, isethionates and taurates. Of these anionic surfactants, it is preferable to use $C_{8-20}$ alkyl carboxylates including fatty acids, $C_{8-20}$ alcohol sulfates, $C_{8-20}$ alcohol phosphate mono- and diesters, $C_{8-20}$ alcohol polyoxyethylene ether carboxylates, sulfates and sulfonates, $C_{8-20}$ alcohol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, and $C_{8-20}$ acyl glutamates, sarcosinates, isethionates and taurates.

In one embodiment, the compositions of the invention may comprise at least one anionic surfactant. In another embodiment, the compositions of the invention may comprise at least two anionic surfactants. In another embodiment, the compositions of the invention may comprise at least three anionic surfactants. In another embodiment, the compositions of the invention may comprise at least four anionic surfactants. The anionic surfactants may be used in the compositions in an amount of about 0.1 to about 8% by weight, preferably in an amount of about 1 to about 4% by weight.

The basic compounds may be any known in the art that are capable of neutralizing the anionic surfactants. Basic compounds include, for example, inorganic bases, $C_{8-18}$ alkyl amine polyalkoxylates, alkanol amines, alkanol amides, and mixtures thereof.

Exemplary inorganic bases include ammonium hydroxides, sodium hydroxides, potassium hydroxides, calcium hydroxides, magnesium hydroxides, zinc hydroxides, and mixtures thereof. The $C_{8-18}$ alkyl amine polyalkoxylates may be, for example, $C_{8-18}$ alkyl amine polypropoxylates and/or $C_{8-18}$ alkyl amine polyethoxylates. Exemplary $C_{8-18}$ alkyl amine polyalkoxylates include tallow amine polyalkoxylates, cocoamine polyalkoxylates, oleylamine polyalkoxylates, and stearylamine polyalkoxylates. The $C_{8-18}$ alkyl amine polyethoxyates may have from about 2 to about 50 moles of ethylene oxide per molecule, more preferably from about 2 to about 20 moles of ethylene oxide per molecule. Exemplary $C_{8-18}$ alkyl amine polyethoxylates include tallow amine ethoxylates (2 moles EO or 8 moles EO), cocoamine ethoxylates, oleylamine ethoxylates, and stearylamine ethoxylates. Exemplary alkanol amines include diethanol amine and triethanol amine. Exemplary alkanol amides include oleic diethanolamide and linoleic diethanolamide, and the diethanolamides of other $C_{8-18}$ fatty acids.

The basic compounds may be used in an amount of about 0.1 to 8% by weight, preferably in an amount of about 0.5 to 4% by weight.

The one or more anionic surfactants are preferably neutralized to the inflection point in the titration curve with the one or more basic compounds. One skilled in the art will recognize that the pH of the inflection will vary according to the acid and base strengths of the components being used, but will generally fall within the range of about pH 4 to about pH 9, preferably about pH 5 to about pH 7. For example, the compositions of the invention may comprise at least one polyarylphenol polyalkoxyether sulfate and/or at least one polyarylphenol polyalkoxyether phosphate neutralized to the inflection point in the titration curve with one or more basic compounds. In other embodiments, the compositions of the invention may comprise at least one anionic surfactant selected from polyarylphenol polyalkoxyether sulfates and polyarylphenol polyalkoxyether phosphates neutralized to the inflection point in the titration curve with one or more basic compounds; and at least one anionic surfactant selected from $C_{8-18}$ alcohol polyalkoxyether phosphates, $C_{8-18}$ alcohol polyalkoxyether carboxylates, $C_{8-18}$ alcohol polyalkoxyether citrates, and alkyl benzenesulfonic acids neutralized to the inflection point in the titration curve with one or more basic compounds. The basic compound used to neutralize the different anionic surfactants may be the same or different. In other embodiments, the compositions of the invention may comprise at least one anionic surfactant selected from polyarylphenol polyalkoxyether sulfates and polyarylphenol polyalkoxyether phosphates neutralized to the inflection point in the titration curve with one or more basic compounds; and at least one anionic surfactant selected from $C_{8-18}$ alcohol polyalkoxyether phosphates, and $C_{8-18}$ alcohol polyalkoxyether citrates neutralized to the inflection point in the titration curve with one or more basic compounds. The basic compound used to neutralize the different anionic surfactants may be the same or different. In still other embodiments, the compositions of the invention comprise at least one anionic surfactant selected from polyarylphenol polyalkoxyether sulfates and polyarylphenol polyalkoxyether phosphates neutralized to the inflection point in the titration curve with one or more basic compounds; and at least one anionic surfactant selected from $C_{8-18}$ alcohol polyalkoxyether carboxylates and alkyl benzenesulfonic acids neutralized to the inflection point in the titration curve with one or more basic compounds. The basic compound used to neutralize the different anionic surfactants may be the same or different.

In still other embodiments, the compositions of the invention comprise at least one anionic surfactant selected from polyarylphenol polyalkoxyether sulfates and polyarylphenol polyalkoxyether phosphates neutralized to the inflection point in the titration curve with one or more basic compounds; and one or more additional anionic surfactants neutralized to the inflection point in the titration curve with one or more basic compounds. The basic compound used to neutralize the different anionic surfactants may be the same or different. Such one or more additional anionic surfactants may include, for example, $C_{8-20}$ alkyl carboxylates including fatty acids, $C_{8-20}$ alcohol sulfates, $C_{8-20}$ alcohol phosphate mono- and diesters, $C_{8-20}$ alcohol and ($C_{8-20}$ alkyl) phenol polyoxyethylene ether carboxylates, sulfates and sulfonates, $C_{8-20}$ alcohol and ($C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, and $C_{8-20}$ acyl glutamates, sarcosinates, isethionates and taurates. Of these one or more additional anionic surfactants, it is preferable to use $C_{8-20}$ alkyl carboxylates including fatty acids, $C_{8-20}$ alcohol sulfates, $C_{8-20}$ alcohol phosphate mono- and diesters, $C_{8-20}$ alcohol polyoxyethylene ether carboxylates, sulfates and sulfonates, $C_{8-20}$ alcohol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, and $C_{8-20}$ acyl glutamates, sarcosinates, isethionates and taurates.

The anionic surfactants and basic compounds are preferably used in a ratio of about 1:1. One basic compound may be used to neutralize one or more anionic surfactants. In other embodiments, more than one basic compound may be used to neutralize one or more anionic surfactants.

The surfactant systems of the invention may optionally further comprise one or more nonionic surfactants. The "nonionic surfactants" are different compounds from the alkyl polyglycosides described herein. Exemplary nonionic surfactants include ethylene oxide-propylene oxide block copolymers, ethylene oxide-butylene oxide block copolymers, $C_{2-6}$ alkyl adducts of ethylene oxide-propylene oxide block copolymers, $C_{2-6}$ alkyl adducts of ethylene oxide-butylene oxide block copolymers, polypropylene glycols, polyethylene glycols, polyarylphenol polyethoxy ethers, polyalkylphenol polyethoxy ethers, polyglycol ether derivatives of saturated fatty acids, polyglycol ether derivatives of unsaturated fatty acids, polyglycol ether derivatives of aliphatic alcohols, polyglycol ether derivatives of cycloaliphatic alcohols, fatty acid esters of polyoxyethylene sorbitan, alkoxylated vegetable oils, alkoxylated acetylenic diols, and mixtures thereof. The ethylene oxide-propylene oxide block copolymers may comprise alkyl ether bases, such as butyl ether, methyl ether, propyl ether, ethyl ether, or mixtures thereof. Commercially available nonionic surfactants include, for example, TOXIMUL® 8320 (Stepan Corporation, Northfield, Ill.) (butyl ether derivative of EO/PO block copolymer) and WITCONOL® NS 500LQ (Crompton Corporation, Greenwich, Conn.) (butyl ether derivative of EO/PO block copolymer).

The nonionic surfactants may be used in an amount of 0 to about 8% by weight. In other embodiments, the nonionic surfactants may be used in an amount of more than 0 to about 8% by weight, preferably in an amount of about 0.1% by weight to about 8% by weight, more preferably in an amount of about 0.5% by weight to about 8% by weight, still more preferably in an amount of about 0.5% by weight to about 3% by weight.

The agriculturally active compound may be any known in the art. The term "agriculturally active" refers to chemicals and biological compositions, such as those described herein, which are effective in killing, preventing, or controlling the growth of undesirable pests, such as, plants, insects, mice, microorganism, algae, fungi, bacteria, and the like. These chemicals may commonly be known as, e.g., insecticides, miticides, bactericides, algaecides, fungicides, nematocides, herbicides and the like. The term may also apply to a compound that controls the growth of plants in a desired fashion (e.g., growth regulator), to a compound which mimics the natural systemic activated resistance response found in plant species (e.g., plant activator) or to a compound that reduces the phytotoxic response to a herbicide (e.g., safener).

Exemplary fungicides and bactericides include azoxystrobin, benalaxyl, benomyl, bitertanol, borax, bromocuonazole, sec-butylamine, captafol, captan, calcium polysulfide, carbendazim, chinomethionat, chlorothalonin, chlozolinate, copper sulfate, cyprodinil, cyproconazole, dichlofluanid, dichlorophen, diclomezine, dicloran, diethofencarb, difenoconazole, dimethomorph, diniconazole, dithianon, epoxiconazole, famoxadone, fenarimol, fenbuconazole, fenfuram, fenpiclonil, fenpropidin, fenpropimorph, fentin, fluazinam, fludioxonil, fluoroimide, fluqinconazole, flusulfamide, flutolanil, folpet, fosetyl, furalaxyl, guazatine, hexachlorobenzene, hexaconazole, hydroxyquinoline sulfate, inibenconazole, iminoctadine, ipconazole, iprodione, kasugamycin, kresoxim-methyl, mancozeb, maneb, mefenoxan, mepanipyrim, mepronil, mercuric chloride, metam, metalaxyl, metconazole, metiram, nabam, nickel bis (dimethyldithiocarbamate), nuarimol, oxadixil, oxine-copper, oxolinic acid, penconazole, pencycuron, phthalide, polyoxin B, procymidone, propamocarb, propiconazole, propineb, pyrifenox, pyroquilon, quintozene, sulfur, tebuconazole, tecloftalam, tecnazene, thiabendazole, thifluzamide, thiophanate-methyl, thiram, tolclofos-methyl, tolylfluanid, triadimefon, triadimenol, triazoxide, trifloxystrobin, triforine, triticonazole, vinclozolin, zineb, ziram, and salts thereof, if appropriate.

Exemplary insecticides include abamectin, acephate, acrinathrin, amitraz, azadirachtin, azamethiphos, azinphos-methyl, azocyclotin, bensultap, bifenthrin, bromopropylate, buprofezin, butoxycarboxim, cartap, chlorfenapyr, chlorfenson, chlorfluazuron, clofentezine, coumaphos, cyfluthrin, beta-cyfluthrin, lambda-cyhalothrin, cypermethrin, alpha-cypermethrin, theta-cypermethrin, cyromazine, DDT, deltamethrin, diafenthiuron, dicofol, dicrotophos, difenthiuron, diflubenzuron, emamectin benzoate, endosulfan, esfenvalerate, etoxazole, fenazaquin, fenbutatin oxide, fenoxycarb, fenpyroximate, fipronil, fluazuron, flucycloxuron, flufenoxuron, taufluvalinate, formetanate, furathiocarb, halofenozide, gamma-HCH, hexaflumuron, hexythiazox, hydramethylnon, hydrogen cyanide, lufenuron, methamidophos, methidathion, methiocarb, methomyl, methoxychlor, mevinphos, milbemectin, monocrotophos, nicotine, nitenpyram, novaluron, omethoate, organophosphorus compounds, oxamyl, oxydemeton-methyl, pentachlorophenol, phosphamidon, pymetrozin, permethrin, profenofos, pyridaben, resmethrin, rotenone, sulfluramid, tebufenozide, tebufenpyrad, tebupirimfos, teflubenzuron, tetrachlorvinphos, tetradifon, tetramethrin, thiamethoxam, thiocyclam, thiodicarb, tralomethrin, trichlorfon, friflumuron, trimethacarb, vamidothion, and salts thereof, if appropriate.

Exemplary herbicides include acetochlor, acifluorfen, aclonifen, acrolein, alachlor, ametryne, amitrole, asulam, atrazine, benazolin, bensulfuron-methyl, bentazon, benzofenap, bialaphos, bifenox, bromacil, bromobutide, bromofenoxim, bromoxynil, butachlor, butafenacil, chlomethoxyfen, chloramben, chloroacetic acid, chlorbromuron, chlorimuron-ethyl, chlorotoluron, chlomitrofen, chlorotoluron, chlorthal-dimethyl, clodinafop, clopyralid, clomeprop, cyanazine, 2,4-D, 2,4-DB, daimuron, dalapon, desmedipham, desmetryn, dicamba, dichlobenil, dichloroprop, diclofop, difenzoquat, diflufenican, dimefuron, dimethachlor, dimethametryn, dimethenamid, dinitramine, diquat, diuron, endothall, ethametsulfuron-methyl, fenac, fenclorim, fenoxaprop, fenoxaprop-ethyl, flamprop-methyl, flazasulfuron, fluazifop, fluazifop-p-butyl, flumetsulam, flumiclorac-penyl, fluoroglycofen, flumetsulam, flumeturon, flumioxazin, flupoxam, flupropanate, fluridone, flurtamone, fomasafen, fosamine, glufosinate, glyphosate, haloxyfop, imazameth, imazamethabenz, imazamox, imazapic, imazapyr, imazaquin, imazethapyr, ioxynil, isoproturon, isoxaben, isoxapyrifop, lactofen, lenacil, linuron, MCPA, MCPB, mecoprop, mefenacet, mesotrione, metazachlor, methabenzthiazuron, methylarsonic acid, metolachlor, metobenzuron, naproanilide, naptalam, neburon, nonanoic acid, norflurazon, oryzalin, oxadiazon, oxyfluorfen, paraquat, phenmedipham, picloram, pretilachlor, prodiamine, prometon, prometryn, propachlor, propazine, propisochlor, propyzamide, pyrazolynate, pyrazosulfuron-ethyl, pyributicarb, pyridate, quinclorac, quizalofop-ethyl, rimsulfuron, siduron, simazine, simetryn, sulfamic acid, 2,3,6-TBA, terbumeton, terbuthylazine, terbutryn, trichloroacetic acid, triclopyr, trietazine, thenylchlor, thiazopyr, tralkoxydim, trietazine, and salts thereof, if appropriate.

Exemplary growth regulators include 6-benzylaminopurine, chlormequat, chlorphonium, cimectacarb, clofencet, cloxyfonac, cyanamide, cyclanilide, daminozide, dikegulac, ethephon, flumetralin, forchlorfenuron, inabenfide, 2-(1-naphthyl)acetamide, mepiquat, paclobutrazol, N-phenylphthalamic acid, thidiazuron, uniconzole, and salts thereof, if appropriate.

Exemplary safeners include benoxacor, cloquintocet, dichlormid, fenclorim, fluxofenime, furilazole, oxabetrinil, and salts thereof, if appropriate.

Exemplary plant activators include acibenzolar-S-methyl, and salts thereof, if appropriate.

In the compositions of the invention, the agriculturally active compounds may be used singly or may be used in combinations of 2, 3, 4, 5, 6, 7 or more. For example, the compositions of the invention may comprise glyphosate; S-metolachlor; atrazine; glufosinate; acetochlor; mesotrione; glyphosate and S-metolachlor; glyphosate, S-metolachlor and atrazine; glyphosate, S-metolachlor, atrazine and benoxacor; S-metolachlor and atrazine; S-metolachlor, atrazine and benoxacor; S-metolachlor, atrazine and butavenacil; S-metolachlor, atrazine, benoxacor and butafenacil; glyphosate, acetochlor and atrazine; glyphosate, S-metolachlor and atrazine; glufosinate, acetochlor and atrazine; glufosinate, S-metolachlor and atrazine; mesotrione and S-metolachlor; mesotrione, S-metolachlor and benoxacor; mesotrione, S-metolachlor and atrazine; mesotrione, S-metolachlor, benoxacor and atrazine; glyphosate and flumioxazin; flumixoazin, glyphosate and flumiclorac; flumiclorac; or any other agriculturally active compounds singly or in combination.

The agriculturally active compounds may be present in the compositions of the invention in an amount of about 1 to about 75% by weight, preferably an amount of about 5 to about 70% by weight, more preferably in an amount of about 10 to about 65% by weight, still more preferably in an amount of about 10 to about 40% by weight. In other embodiments, the agriculturally active compounds may be present in the compositions of the invention in an amount of about 50 to about 65% by weight. It has been unexpectedly discovered that a broad range of agriculturally active compounds may be used in the compositions of the invention to provide stable compositions. For example, the agriculturally active compounds may be water-soluble, oil-soluble, or insoluble in water and oil. Thus, the compositions of the invention may contain agriculturally active compounds that are water-soluble, oil/solvent-soluble, and/or insoluble in water and oil/solvent. The agriculturally active compounds may be present in the compositions of the invention in the form of, for example, finely dispersed solids. In other embodiments, the agriculturally active compounds may be dispersed in a liquid phase.

The agricultural compositions and surfactant systems of the invention may further comprise other inert additives. Such additives include thickeners, flow enhancers, wetting agents, antifoaming agents, buffers, lubricants, fillers, drift control agents, deposition enhancers, adjuvants, evaporation retardants, frost protecting agents, insect attracting odor agents, UV protecting agents, fragrances, and the like. The thickener may be a compound that is soluble or able to swell in water, such as, for example, polysaccharides of xanthans (e.g., anionic heteropolysaccharides), alignates, guars or celluloses; synthetic macromolecules, such as polyethylene glycols, polyvinyl pyrrolidones, polyvinyl alcohols, poly- carboxylates of swellable structure-forming silicates such as pyrogenic or precipitated silicic acids, bentonites, montmorillonites, hectonites, or attapulgites; or organic derivatives of aluminum silicates. The frost protecting agent may be, for example, ethylene glycol, propylene glycol, glycerol, diethylene glycol, triethylene glycol, tetraethylene glycol, urea, or mixtures thereof. The antifoaming agent may be, for example, a polydimethylsiloxane.

For water-based products, the surfactant systems of the invention may be made by combining water-soluble surfactants, water-soluble agriculturally active compounds, water-insoluble solid agriculturally active compounds and water. If a water-insoluble solid agriculturally active compound is present, milling a slurry of the agriculturally active compound, water, defoamer, and all or a portion of the water soluble surfactants may be indicated to achieve the desired particle size. The particle size may be an average particle size of about 1 to about 20 microns, preferably about 1 to about 15 microns, more preferably about 2 to about 10 microns.

For oil-based products, the surfactant systems of the invention may be made by combining the oil soluble surfactants with oily liquid agriculturally active compounds, oil miscible/oil soluble solvents, and oil insoluble solid agriculturally active compounds. If an oil insoluble solid agriculturally active compound is present, it may be necessary to mill a slurry of the agriculturally active compound, an oil or solvent, and a portion or all of the oil soluble surfactants to obtain the desired particle size. The particle size may be an average particle size of about 1 to about 20 microns, preferably about 1 to about 15 microns, more preferably about 2 to about 10 microns.

Methods for making the surfactant systems of the invention are also described in Examples 1–4.

It has also been unexpectedly discovered that the agricultural compositions and surfactant systems of the invention may be mixed with water to form stable suspoemulsions. For example, stable suspoemulsions will be formed in very soft water (i.e., water containing 0 ppm calcium carbonate equivalent) to very hard water (e.g., water containing over 2,000 ppm calcium carbonate equivalent). Suspoemulsions have a liquid aqueous phase, which is generally a continuous phase, a liquid oil phase, which is generally a discontinuous phase dispersed in the aqueous phase, and a solid particulate phase, which is a discontinuous phase dispersed in one or both of the liquid phases.

The surfactant systems and agricultural compositions of the invention may be used as flowable concentrates (which include suspoemulsions, aqueous suspension concentrates, aqueous emulsion concentrates, and oil miscible flowable concentrates), water-in-oil emulsions, capsule emulsions and polymer-stabilized emulsions. Flowable concentrates are often used for seed treatments.

It has also been unexpectedly discovered that the compositions of the invention may be mixed with fertilizers and maintain their stability. For example, when the compositions of the invention are mixed with fertilizers, they do not exhibit any visible flocculation after about one hour. The fertilizers may comprise, for example, nitrogen, phosphorous, and/or potassium. In one embodiment, the fertilizer may be 10-34-0 fertilizer.

The agricultural compositions and surfactant systems of the invention may be used in conventional agricultural methods. For example, the agricultural compositions and surfactant systems of the invention may be mixed with water and/or fertilizers and may be applied preemergence and/or postemergence to a desired locus by any means, such as airplane spray tanks, knapsack spray tanks, cattle dipping vats, farm equipment used in ground spraying (e.g., boom sprayers, hand sprayers), and the like. The desired locus may be soil, plants, and the like. The term "plants" includes seeds, seedlings, saplings, roots, tubers, stems, stalks, foliage and fruits.

EXAMPLES

The following examples are for purposes of illustration only and are not intended to limit the scope of the appended claims.

Generally, the compositions in the examples were prepared by first preparing a series of premixes and blending the premixes to prepare the final composition. Glyphosate isopropylamine salt was used as a 62% solution in water. Atrazine was used in a finely ground, commercially-available form (i.e., more than 98% of the particles are less than 44 microns in diameter). In the examples, the percentages are percentages by weight.

Example 1

A composition was prepared with the following components:
- 53.2% agriculturally active compounds (comprising 22.9% atrazine, 18.7% S-metolachlor, 0.9% benoxacor, and 10.8% glyphosate isopropylamine salt);
- 2.3% tristyrylphenol polyethoxyether phosphate (SOPROPHOR® 3D33);
- 0.7% tallow amine ethoxylate (2 moles EO) (TOXIMUL® TA-2);
- 2.0% alkyl polyglycoside (AGRIMUL® PG 2067);
- 1.0% dodecylbenzene sulfonic acid (BIOSOFT® S-101);
- 0.5% tallow amine ethoxylate (8 moles EO) (WITCAMINE® TAM-80);
- 0.1% anionic heteropolysaccharide (RHODOPOL® 23);
- 0.05% 1,2-benzisothiazolin-3-one (PROXEL® GXL);
- 0.3% polydimethylsiloxane (Dow Corning Antifoam 1500); and
- 39.85% water.

An aqueous premix was prepared by stirring together 23 grams of SOPROPHOR® 3D33 with 7 grams of TOXIMUL® TA-2, next adding 242.8 grams of water, and then adding 229 grams of technical atrazine. Stirring was continued until a uniform, fluid slurry was obtained.

An S-metolachlor/benoxacor premix was made by allowing 9 grams of benoxacor to dissolve into 187 grams of s-metolachlor. Thereafter, 10 grams of BIOSOFT® S-101 and 5 grams of WITCAMINE® TAM-80 were added and stirred until totally dissolved.

The S-metolachlor premix and the aqueous premix were blended together simultaneously with good agitation.

A solution was made from 108 grams glyphosate isopropylamine salt in 66 grams of water. This was then added to the previous mixture. Next, 20 grams of AGRIMUL® PG 2067 was added to the mixture.

With good agitation, a dispersion of 1 gram of RHODOPOL® 23 and 0.5 grams of PROXEL® GXL were prepared in 88.7 grams of water. The mixture was agitated until full swelling of the RHODOPOL® 23 occurred. This dispersion was then added with stirring to the mixture previously described. To control foaming, 3 grams of Dow Corning Antifoam 1500 was added.

The resulting composition exhibited good physical stability and fertilizer compatibility.

Example 2

A composition was prepared with the following components:
- 64.4% agriculturally active compounds (comprising 16.2% atrazine, 42.2% S-metolachlor, 2.1% benoxacor, 3.9% butafenacil);
- 0.9% tristyrylphenol polyethoxyether phosphate (SOPROPHOR® 3D33);
- 3.3% alkyl polyglycoside (AGRIMUL® PG 2069);
- 1.5% butanol copolymer PO/EO (TOXIMUL® 8320);
- 0.8% tridecyl alcohol polyethoxyether phosphate (STEPFAC® 8181);
- 1% mixture of tristyrylphenol (EO) 8 sulfate and tallowamine (EO) 5 (DV-4636);
- 1.5% linoleic diethanolamide (WITCAMIDE® 511);
- 2.0% ethylene glycol;
- 0.03% anionic heteropolysaccharide (RHODOPOL® 23);
- 0.03% 1,2-benzisothiazolin-3-one (PROXEL® GXL);
- 0.1% polydimethylsiloxane (Dow Corning Antifoam 1500); and
- 24.44% water.

An aqueous premix was made by slurrying together 9 grams of SOPROPHOR® 3D33, 8 grams of STEPFAC® 8181, 15 grams of WITCAMIDE® 511, and 20 grams of ethylene glycol. Next, 200 grams of water was added and stirred until uniform. Then, 162 grams of technical atrazine was added and the premix was stirred until uniform.

An S-metolachlor premix was made by allowing 21 grams of benoxacor and 39 grams of butafenacil to dissolve into 422 grams of S-metolachlor. To this solution, 15 grams of TOXIMUL® 8320 and 10 grams of DV-4636 were added and allowed to mix until uniform.

The aqueous premix and the S-metolachlor premix were blended together until uniform using good agitation. To this mixture, 33 grams of AGRIMUL® PG-2069 were added.

An aqueous pregel was prepared by adding 0.3 grams of RHODOPOL® 23 and 0.3 grams of PROXEL® GXL to 44.4 grams of water with vigorous agitation. Agitation was continued until the RHODOPOL® 23 achieved full swelling. This mixture was added to the mixture previously described. 1 gram of Dow Coring Antifoam 1500 was added to control foaming.

The resulting composition exhibited good physical stability and fertilizer compatibility.

Example 3

A composition was prepared with the following components:
- 57.3% agriculturally active compounds (comprising 28.6% atrazine; 24.9% S-metolachlor; 1.2% benoxacor; 2.6% butafenacil);
- 0.9% tristyrylphenol polyethoxyether phosphate (SOPROPHOR® 3D33);
- 3.3% alkyl polyglycoside (AGRIMUL® PG 2069);
- 1.5% butanol copolymer PO/EO (TOXIMUL® 8320);
- 0.8% tridecyl alcohol polyethoxyether phosphate (STEPFAC® 8181);
- 1% mixture of tristyrylphenol (EO) 8 sulfate and tallowamine (EO) 5 (DV-4636);
- 1.5% linoleic diethanolamide (WITCAMIDE® 511);
- 2.0% ethylene glycol;
- 0.03% anionic heteropolysaccharide (RHODOPOL® 23)

0.03% 1,2-benzisothiazolin-3-one (PROXEL® GXL);

0.1% polydimethylsiloxane (Dow Corning Antifoam 1500); and 31.54% water.

An aqueous premix was prepared by mixing 9 grams of SOPROPHOR® 3D33, 8 grams of STEPFAC® 8181, 15 grams of WITCAMIDE® 511, and 20 grams of ethylene glycol. This mixture was stirred until uniform. Next, 300 grams of water were added, followed by the addition of 286 grams of atrazine technical.

An S-metolachlor premix was made by allowing 12 grams of benoxacor and 26 grams of butafenacil to dissolve into 249 grams of S-metolachlor. Next 15 grams of TOXIMUL® 8320 and 10 grams of DV-4636 were added.

The aqueous premix was added to the S-metolachlor premix with continuous stirring and was blended until uniform. Next, 33 grams of AGRIMUL® PG 2069 were added.

An aqueous pregel was prepared by adding 0.3 grams of RHODOPOL(D 23 and 0.3 grams of PROXEL® GXL to 15.4 grams of water. The aqueous pregel was added to the mixture previously described. 1 gram of Dow Corning Antifoam 1500 was added to control foaming.

The resulting composition exhibited good physical stability and fertilizer compatibility.

Example 4

A composition was prepared with the following components:

61.11% agriculturally active compounds (comprising 33.7% atrazine technical; 26.1% S-metolachlor and 1.31% benoxacor);

1.7% tridecyl alcohol (EO) 6 phosphate (STEPFAC® 8181);

1% tallowamine (EO) 2 (TOXIMUL® TA-2);

0.3% mixture of tristyrylphenol (EO) 8 sulfate and tallowamine (EO) 5 (DV-4636);

0.3% tristyrylphenol (EO) 25 (SOPROPHOR® S-25);

1.8% butoxy EO/PO block copolymer (WITCONOL® NS500LQ);

1% alkylpolyglycoside ($C_{9-11}$) (AGRIMUL® PG2069);

1% attapulgite clay (ATTAFLOW® FL);

0.67% tridecyl alcohol (EO) 6 (RENEX® 36);

0.22% EO/PO block polymer (STEPFAC® 8323);

1.75% ethylene glycol;

0.1% silicone-based oil (Antifoam A);

0.03% 1,2-benzisothiazolin-3-one (PROXEL® GXL);

0.03% xantham gum (RHODOPOL® 23);

28.99% water.

An aqueous premix was made by mixing 200 grams of water with 6.7 grams of RENEX® 36, 2.2 grams STEPFAC® 8323, 1 gram of Antifoam A and 17.5 grams of ethylene glycol. Next, 337 grams of technical atrazine were added. The mixture was blended until uniform.

An S-metolachlor premix was made by allowing 13.1 grams of benoxacor to dissolve into 261 grams of S-metolachlor. Then, 17 grams of STEPFAC® 8181, 10 grams of TOXIMUL® TA-2, 3 grams of DV-4636, 18 grams of WITCONOL® NS500LQ, and 3 grams of SOPROPHOR® S-25 were added with continuous mixing.

The S-metolachlor premix was added to the aqueous premix and blended until uniform.

An aqueous pregel was prepared by adding 0.3 grams of PROXEL® GXL and 0.3 grams of RHODOPOL® 23 to 89.9 grams of water. The mixture was agitated vigorously until the RHODOPOL® 23 swelled completely. The aqueous pregel was added to the mixture described in the previous paragraph. 10 grams of AGRIMUL® PG2069 and 10 grams of ATTAFLOW® FL were added to complete the formulation.

The resulting composition exhibited good physical stability and fertilizer compatibility.

Each of the patents and publications cited herein are incorporated by reference herein in their entirety.

It will be apparent to one skilled in the art that various modifications can be made to the invention without departing from the spirit or scope of the appended claims

What is claimed is:

1. An agricultural composition comprising
    at least one agriculturally active compound;
    at least one alkyl polyglycoside;
    at least one anionic surfactant selected from a polyarylphenol polyalkoxyether sulfate and a polyarylphenol polyalkoxyether phosphate; and
    at least one basic compound;
    wherein the at least one anionic surfactant is neutralized to the inflection point in the titration curve with the at least one basic compound.

2. The agricultural composition of claim 1, further comprising at least one nonionic surfactant.

3. The agricultural composition of claim 1, wherein the polyarylphenol polyalkoxyether sulfate is a polyarylphenol polyethoxyether sulfate and the polyarylphenol polyalkoxyether phosphate is a polyarylphenol polyethoxyether phosphate.

4. The agricultural composition of claim 3, wherein the polyarylphenol polyethoxyether sulfate is a tristyrylphenol polyethoxyether sulfate, and the polyarylphenol polyethoxyether phosphate is a tristyrylphenol polyethoxyether phosphate.

5. The agricultural composition of claim 1, wherein the alkyl polyglycoside is a compound of formula (I):

$$R_1O(R_2O)_b(Z)_a \qquad (I)$$

wherein $R_1$ is a monovalent organic radical having from about 6 to about 30 carbon atoms; $R_2$ is a divalent alkylene radical having from about 2 to about 4 carbon atoms; b is 0 to about 100; Z is a saccharide residue having about 5 to about 6 carbon atoms; and a is an integer from about 1 to about 6.

6. The agricultural composition of claim 5, wherein $R_1$ is a $C_{8-11}$ alkyl group, b is 0, a is 2, and Z is glucose.

7. The agricultural composition of claim 1, wherein the basic compound is an inorganic base, a $C_{8-18}$ alkyl amine polyalkoxylate, an alkanol amine, an alkanol amide, or a mixture thereof.

8. The agricultural composition of claim 1, wherein the basic compound is a tallow amine ethoxylate, a cocoamine alkoxylate, a oleylamine alkoxylate, a stearylamine alkoxylate, a linoleic diethanolamide, or a mixture thereof.

9. The agricultural composition of claim 2, wherein the nonionic surfactant is an ethylene oxide-propylene oxide block copolymer, ethylene oxide-butylene oxide block copolymer, a $C_{2-6}$ alkyl adduct of an ethylene oxide-propylene oxide block copolymer, a $C_{2-6}$ alkyl adduct of an ethylene oxide-butylene oxide block copolymer, a polypropylene glycol, a polyethylene glycol, a polyarylphenol polyethoxy ether, a polyalkylphenol polyethoxy ether, a polyglycol ether derivative of a saturated fatty acid, a polyglycol ether derivative of an unsaturated fatty acid, a polyglycol ether derivative of an aliphatic alcohol, a polyglycol ether derivative of a cycloaliphatic alcohol, a fatty acid ester of polyoxyethylene sorbitan, an alkoxylated vegetable oil, an alkoxylated acetylenic diol, or a mixture thereof.

10. The agricultural composition of claim 1, wherein the at least one agriculturally active compound is present in an amount of about 1 to about 75% by weight; the at least one alkyl polyglycoside is present in an amount of about 0.1 to about 8% by weight; the at least one anionic surfactant is present in an amount of about 0.1 to about 8% by weight; and the at least one basic compound is present in an amount of about 0.1 to about 8% by weight.

11. The agricultural composition of claim 10, wherein the at least one agriculturally active compound is present in an amount of about 15 to about 70% by weight; the at least one alkyl glycoside is present in an amount of about 1 to about 4% by weight; the at least one anionic surfactant is present in an amount of about 1 to about 4% by weight; and the at least one basic compound is present in an amount of about 0.5 to about 4% by weight.

12. The agricultural composition of claim 2, wherein the at least one agriculturally active compound is present in an amount of about 1 to about 75% by weight; the at least one alkyl polyglycoside is present in an amount of about 0.1 to about 8% by weight; the at least one anionic surfactant is present in an amount of about 0.1 to about 8% by weight; the at least one basic compound is present in an amount of about 0.1 to about 8% by weight; and the at least one nonionic surfactant is present in an amount of about 0.1 to about 8% by weight.

13. The agricultural composition of claim 12, wherein the at least one agriculturally active compound is present in an amount of about 15 to about 70% by weight; the at least one alkyl glycoside is present in an amount of about 1 to about 4% by weight; the at least one anionic surfactant is present in an amount of about 1 to about 4% by weight; the at least one basic compound is present in an amount of about 0.5 to about 4% by weight; and the at least one nonionic surfactant is present in an amount of about 0.5 to about 3% by weight.

14. The agricultural composition of claim 1, wherein the at least one agriculturally active compound is glyphosate; S-metolachlor; atrazine; glufosinate; acetochlor; mesotrione; glyphosate and S-metolachlor; glyphosate, S-metolachlor and atrazine; glyphosate, S-metolachlor, atrazine and benoxacor; S-metolachlor and atrazine; S-metolachlor, atrazine and benoxacor; S-metolachlor, atrazine and butavenacil; S-metolachlor, atrazine, benoxacor and butafenacil; glyphosate, acetochlor and atrazine; glyphosate, S-metolachlor and atrazine; glufosinate, acetochlor and atrazine; glufosinate, S-metolachlor and atrazine; mesotrione and S-metolachlor; mesotrione, S-metolachlor and benoxacor; mesotrione, S-metolachlor and atrazine; or mesotrione, S-metolachlor, benoxacor and atrazine.

15. The agricultural composition of claim 1, wherein the agriculturally active compound is a fungicide, an insecticide, an herbicide, a growth regulator, a safener, a plant activator, or a mixture thereof.

16. The agricultural composition of claim 15, wherein the fungicide is azoxystrobin, benalaxyl, benomyl, bitertanol, borax, bromocuonazole, sec-butylamine, captafol, captan, calcium polysulfide, carbendazim, chinomethionat, chlorothalonin, chlozolinate, copper sulfate, cyprodinil, cyproconazole, dichlofluanid, dichlorophen, diclomezine, dicloran, diethofencarb, difenoconazole, dimethomorph, diniconazole, dithianon, epoxiconazole, famoxadone, fenarimol, fenbuconazole, fenfuram, fenpiclonil, fenpropidin, fenpropimorph, fentin, fluazinam, fludioxonil, fluoroimide, fluqinconazole, flusulfamide, flutolanil, folpet, fosetyl, furalaxyl, guazatine, hexachlorobenzene, hexaconazole, hydroxyquinoline sulfate, imibenconazole, iminoctadine, ipconazole, iprodione, kasugamycin, kresoxim-methyl, mancozeb, maneb, mefenoxam, mepanipyrim, mepronil, mercuric chloride, metam, metalaxyl, metconazole, metiram, nabam, nickel bis (dimethyldithiocarbamate), nuarimol, oxadixil, oxine-copper, oxolinic acid, penconazole, pencycuron, phthalide, polyoxin B, procymidone, propamocarb, propiconazole, propineb, pyrifenox, pyroquilon, quintozene, sulfur, tebuconazole, tecloftalam, tecnazene, thiabendazole, thifluzamide, thiophanate-methyl, thiram, tolclofos-methyl, tolylfluanid, triadimefon, triadimenol, triazoxide, trifloxystrobin, triforine, triticonazole, vinclozolin, zineb, ziram, salts thereof, or a mixture thereof.

17. The agricultural composition of claim 15, wherein the insecticide is abamectin, acephate, acrinathrin, amitraz, azadirachtin, azamethiphos, azinphos-methyl, azocyclotin, bensultap, bifenthrin, bromopropylate, buprofezin, butoxycarboxim, cartap, chlorfenapyr, chlorfenson, chlorfluazuron, clofentezine, coumaphos, cyfluthrin, beta-cyfluthrin, lambda-cyhalothrin, cypermethrin, alpha-cypermethrin, theta-cypermethrin, cyromazine, DDT, deltamethrin, diafenthiuron, dicofol, dicrotophos, difenthiuron, diflubenzuron, emamectin benzoate, endosulfan, esfenvalerate, etoxazole, fenazaquin, fenbutatin oxide, fenoxycarb, fenpyroximate, fipronil, fluazuron, flucycloxuron, flufenoxuron, tau-fluvalinate, formetanate, furathiocarb, halofenozide, gamma-HCH, hexaflumuron, hexythiazox, hydramethylnon, hydrogen cyanide, lufenuron, methamidophos, methidathion, methiocarb, methomyl, methoxychlor, mevinphos, milbemectin, monocrotophos, nicotine, nitenpyram, novaluron, omethoate, organophosphorus compounds, oxamyl, oxydemeton-methyl, pentachlorophenol, phosphamidon, pymetrozin, permethrin, profenofos, pyridaben, resmethrin, rotenone, sulfluramid, tebufenozide, tebufenpyrad, tebupirimfos, teflubenzuron, tetrachlorvinphos, tetradifon, tetramethrin, thiamethoxam, thiocyclam, thiodicarb, tralomethrin, trichlorfon, friflumuron, trimethacarb, vamidothion, and salts thereof, or a mixture thereof.

18. The agricultural composition of claim 15, wherein the herbicide is acetochlor, acifluorfen, aclonifen, acrolein, alachlor, ametryne, amitrole, asulam, atrazine, benazolin, bensulfuron-methyl, bentazon, benzofenap, bialaphos, bifenox, bromacil, bromobutide, bromofenoxim, bromoxynil, butachlor, butafenacil, chlomethoxyfen, chloramben, chloroacetic acid, chlorbromuron, chlorimuron-ethyl, chlorotoluron, chlomitrofen, chlorotoluron, chlorthal-dimethyl, clodinafop, clopyralid, clomeprop, cyanazine, 2,4-D, 2,4-DB, daimuron, dalapon, desmedipham, desmetryn, dicamba, dichlobenil, dichloroprop, diclofop, difenzoquat, diflufenican, dimefuron, dimethachlor, dimethametryn, dimethenamid, dinitramine, diquat, diuron, endothall, ethametsulfuron-methyl, fenac, fenclorim, fenoxaprop, fenoxaprop-ethyl, flamprop-methyl, flazasulfuron, fluazifop, fluazifop-p-butyl, flumetsulam, flumiclorac-penyl, fluoroglycofen, flumetsulam, flumeturon, flumioxazin, flupoxam, flupropanate, fluridone, flurtamone, fomasafen, fosamine, glufosinate, glyphosate, haloxyfop, imazameth, imazamethabenz, imazamox, imazapic, imazapyr, imazaquin, imazethapyr, ioxynil, isoproturon, isoxaben, isoxapyrifop, lactofen, lenacil, linuron, MCPA, MCPB, mecoprop, mefenacet, mesotrione, metazachlor, methabenzthiazuron, methylarsonic acid, metolachlor, metobenzuron, naproanilide, naptalam, neburon, nonanoic acid, norflurazon, oryzalin, oxadiazon, oxyfluorfen, paraquat, phenmedipham, picloram, pretilachlor, prodiamine, prometon, prometryn, propachlor, propazine, propisochlor, propyzamide, pyrazolynate, pyrazosulfuron-ethyl, pyributicarb, pyridate, quinclorac, quizalofop-ethyl, rimsulfuron, siduron, simazine, simetryn, sulfamic acid, 2,3,6-TBA, terbumeton, terbuthylazine, terbutryn, trichloroacetic acid, triclopyr, trietazine, thenylchlor, thiazopyr, tralkoxydim, trietazine, salts thereof, or a mixture thereof.

19. The agricultural composition of claim 15, wherein the growth regulator is 6-benzylaminopurine, chlormequat, chlorphonium, cimectacarb, clofencet, cloxyfonac, cyanamide, cyclanilide, daminozide, dikegulac, ethephon, flumetralin, forchlorfenuron, inabenfide, 2-(1-naphthyl) acetamide, mepiquat, paclobutrazol, N-phenylphthalamic acid, thidiazuron, uniconzole, salts thereof, or a mixture thereof.

20. The agricultural composition of claim 15, wherein the safener is benoxacor, cloquintocet, dichlormid, fenclorim, fluxofenime, furilazole, oxabetrinil, salts thereof, or a mixture thereof.

21. The agricultural composition of claim 15, wherein the plant activator is acibenzolar-S-methyl.

22. The agricultural composition of claim 1, further comprising water.

23. The agricultural composition of claim 1, further comprising a thickener.

24. The agricultural composition of claim 1, further comprising an anti-foaming agent.

25. The agricultural composition of claim 1, further comprising a frost protecting agent.

* * * * *